United States Patent [19]

Seidler et al.

[11] 4,278,607
[45] Jul. 14, 1981

[54] PROCESS FOR THE PREPARATION OF DIMETHOXYANTHRAQUINONES

[75] Inventors: Helmut Seidler, Bonn; Günter Gehrke, Cologne, both of Fed. Rep. of Germany

[73] Assignee: Bayer Aktiengesellschaft, Leverkusen, Fed. Rep. of Germany

[21] Appl. No.: 110,877

[22] Filed: Jan. 10, 1980

[30] Foreign Application Priority Data

Feb. 1, 1979 [DE] Fed. Rep. of Germany ....... 2903851

[51] Int. Cl.$^3$ .............................................. C07C 49/74
[52] U.S. Cl. ..................................... 260/383; 260/378
[58] Field of Search ................................. 260/378, 383

[56] References Cited

U.S. PATENT DOCUMENTS 4,080,370  3/1978  Kimura et al. ....................... 260/383

FOREIGN PATENT DOCUMENTS 2314696 10/1974 Fed. Rep. of Germany ........... 260/383
2607036  9/1976 Fed. Rep. of Germany ........... 260/383

*Primary Examiner*—Patrick Garvin
*Assistant Examiner*—Raymond K. Covington
*Attorney, Agent, or Firm*—Sprung, Felfe, Horn, Lynch & Kramer

[57] ABSTRACT

Dimethoxyanthraquinones can be prepared in high purity and in good yield in an economic manner which does not pollute the environment when 1 part by weight of dinitroanthraquinone is reacted with 2-8 parts by weight of methanol and 0.5-1.5 parts by weight of potassium hydroxide until all of the nitro groups have been replaced; the reaction is preferably carried out in the presence of 0.05-0.5 part by weight of amidosulphonic acid.

7 Claims, No Drawings

PROCESS FOR THE PREPARATION OF DIMETHOXYANTHRAQUINONES

The present invention relates to a process for the preparation of dimethoxyanthraquinones by reacting dinitroanthraquinones with methanol in the presence of potassium hydroxide.

Several processes for the preparation of dimethoxyanthraquinones from corresponding dinitroanthraquinones are already described in the literature.

In German Patent Specification No. 77,818, mixtures of dinitroanthraquinones which are obtained by nitrating anthraquinone with nitric acid-/sulphuric acid mixtures are reacted, in methanolic suspension, with alkali metal hydroxides or alkaline earth metal hydroxides. However, about 30–40% of by-products, such as aminoanthraquinones and hydroxyanthraquinones, inter alia, are obtained in this reaction (in this context, compare the appropriate statements in DOS (German Published Specification) No. 2,607,036, page 2).

German Offenlegungschrift (German Published Specification) No. 2,152,991 describes a process for the preparation of 1,5- and 1,8-dimethoxyanthraquinone or mixtures thereof, which consists in heating 1,5- and/or 1,8-dinitroanthraquinone with potassium hydroxide in methanol. In DOS (German Published Specification) No. 2,607,036, page 2, it is established that even this process does not prevent side reactions to an adequate extent, so that 10–20% by weight of by-products are still formed. Moreover, the process has the disadvantage that long reaction times of between 18 and 50 hours are required to complete the reaction. The method of working up used, comprising dilution with water and subsequent filtration, is also a disadvantage. The methanol/water mixtures thereby obtained cannot be released into the effluent without expensive working up processes.

DOS (German Published Specification) No. 2,314,696 describes a further process for the preparation of α-methyl ethers of anthraquinone, in which α-nitroanthraquinones are reacted with excess methanol in the presence of potassium carbonate. The $N_2$ content of the products is given exclusively as the criterion for the quality of the reaction products under these conditions, whilst precise analytical data regarding the composition of the products are lacking. Accordingly, in DOS (German Published Specification )No. 2,607,036, page 2, it is logically stated that the $N_2$ contents of the reaction products of less than 0.5% indicated in DOS (German Published Specification) No. 2,314,696 correspond to contents of about 10% of by-products (mainly aminoanthraquinone).

Finally, DOS (German Published Specification) No. 2,607,036 and Japanese Patent Specification No. 53,101,355 claim a process for the preparation of methoxyanthraquinones by reacting nitroanthraquinones with methanol and an alkali metal in a medium consisting predominantly of methanol. In this process, the gaseous, molecular oxygen is fed to the reaction mixture. The disadvantages of this process are apparent: reaction times of 35 hours are required and can be reduced only by adding a further solvent.

The supply of oxygen signifies a safety risk since there is the danger of an explosion, which is pointed out in the patent specification itself, on page 6.

The object of the present invention was thus to discover a process for the preparation of dimethoxyanthraquinones by reaction of corresponding dinitroanthraquinones, which avoids the deficiencies and disadvantages known from the literature already described and is carried out in an economic manner which does not pollute the environment and produces high purities and yields. Furthermore, the new process should not involve a safety risk.

It has now been found that dimethoxyanthraquinones or mixtures thereof can be obtained in high yields and in high purity when the reaction of the dinitroanthraquinones with potassium hydroxide in methanol is carried out in a manner such that 1 part of dinitroantraquinone is reacted with 2–8 parts of methanol and 0.5–1.5 parts of potassium hydroxide, "parts" denoting parts by weight.

Surprisingly, it was found that the formation of by-products, such as was adequately known from the literature described above, can be virtually completely suppressed if amidosulphonic acid is added to the reaction mixture. In addition, it has proved favourable to carry out the reaction at below the boiling point of methanol; under these conditions, virtually no aminoanthraquinones and hydroxyanthraquinones are formed.

In carrying out the process in practice, a procedure is appropriately followed in which 1 part of dinitroanthraquinone is reacted, in 2–8, preferably 3–5 parts of methanol, with 0.5–1.5, preferably 0.6–0.8, part of potassium hydroxide in the presence of 0.05–0.5, preferably 0.1–0.3, part of amidosulphonic acid.

Sometimes it proves favourable to add 0.01 to 0.06 part, preferably 0.02 to 0.04 part, of a commercially available emulsifier to the reaction mixture in order to achieve complete conversion.

1.5- or 1,8-dinitroanthraquinone or mixtures thereof are preferably employed in the process according to the invention. However, the process according to the invention can also be carried out with industrial dinitroanthraquinone mixtures such as are obtained on industrial dinitration of anthraquinone. Such mixtures are described, for example, in OS (Published Specification) No. 2,637,733 and are called 1,X- or X,Y-dinitroanthraguinone, since they also contain α,β- and β,β-dinitroanthroanthraquinones.

The rection temperature can be between 50° and 90° C. if the reaction is carried out under atmospheric pressure, and the reaction has as a rule ended after 5–15 hours. If the reaction is carried out under pressure, higher temperature, for example 90°–150° C., are also possible, in which case pressures of 4–10 atmosphere are established and the reaction has as a rule ended after 3–5 hours.

However, it is particularly preferable to carry out the process according to the invention at temperatures of 60°–70° C.

The end of the reaction is appropriately determined by chromatography. For this, a sample which has been removed from the reaction mixture and worked up is investigated for nitroanthraquinones by thin layer chromatography. At the end of the reaction, residual contents of nitroanthraquinones of $<<1\%$ by weight are present. The reaction mixture contains virtually no by-products such as aminoanthraquinones or hydroxyanthraquinones.

There are several possibilities for isolating the reaction products. It is most economical for the reaction product, which in general is well crystallised, to be separated off from the methanol by filtration. The methanol filtrate can then be passed to a suitable rectification and pure methanol is recovered; however, some of it can also be recycled, undistilled, into the reaction.

A further possibility for working up consists in evaporating the entire reaction mixture, methanol which can be re-used being obtained.

The residues from the filtration or evaporation contain the dimethoxyanthraquinone and also the potassium nitrite formed during the reaction. An after treatment in an aqueous medium containing amidosulphonic acid thus follows, to separate off the potassium nitrite, and the product is then filtered off, washed and dried.

A further possibility for working up consists in dissolving the potassium nitrite out of the residue from the filtration by washing the residue with water and thus to obtain, after drying, the highly pure dimethoxyanthraquinone directly.

From the working up processes described, dimethoxyanthraquinones are obtained with contents of >94%, unreacted dinitroanthraquinones are present in residual contents of <1% and by-products, such as aminoanthraquinones and hydroxyanthraquinones, are virtually undetectable. The yields, relative to dinitroanthraquinone employed, are 90 to 99% of theory.

The dimethoxyanthraquinones, or mixtures thereof, prepared by the process according to the invention are valuable dyestuff intermediate products. A number of industrial dyestuffs for dyeing polyester and wool can be prepared from these products by reactions customary in dyestuff chemistry, such as saponification, nitration, reduction and bromination.

The process according to the invention will be illustrated in more detail by the following examples. The quality data are based on quantitative column chromatography.

EXAMPLE 1

100 parts of 1,5-dinitroanthraquinone (98% pure) are stirred in 160 parts of methanol. A solution of 70 parts of potassium hydroxide in 160 parts of methanol is then allowed to run into the suspension, whilst stirring. After adding 10 parts of amidosulphonic acid, the mixture is heated to 68° C. for about 13 hours, whilst stirring. After it has been proved, in a sample, that the reaction is complete, the batch is concentrated to dryness in a rotary evaporator. The residue is stirred in 1,000 parts of water and the mixture is introduced into a solution of 70 parts of amidosulphonic acid in 1,000 parts of water. After filtering off, washing with water and drying the solid, 89 parts of a 1,5-dimethoxyanthraquinone with a content of 95.4% are obtained. The content of 1-amino-5-methoxyanthraquinone is less than 0.3%. This corresponds to a yield of 97% of theory. The methanol obtained during the distillation can be re-used; the aqueous filtrate from the treatment with amidosulphonic acid is absolutely harmless.

EXAMPLE 2

If the procedure followed is as described in Example 1 and, when the reaction has ended, the solid is isolated by filtration, washing with water and drying, 88 parts of a yellow solid containing 99% of 1,5-dimethoxyanthraquinone are obtained. This corresponds to a yield of 99% of theory. Virtually no nitroanthraquinones and aminoanthraquinones can be detected.

The methanolic mother liquor is worked up by distillation, the methanol being recovered, and after destroying the potassium nitrite with amidosulphonic acid, the washing filtrate is harmless.

EXAMPLE 3

A mixture of 100 parts of 1,5-dinitroanthraquinone (98% pure), 320 parts of methanol, 70 parts of potassium hydroxide and 10 parts of amidosulphonic acid is warmed to 63° C. for 17 hours, whilst stirring. When the reaction has ended, the reaction mixture is cooled and the solid is isolated by filtration. The residue is washed with water and dried. 88 parts of a yellow product which has crystallised as well-formed needles and contains 99% of 1,5-dimethoxyanthraquinone are obtained. The yield is thus 99% of theory. Virtually no nitroanthraquinones and aminoanthraquinones can be detected.

EXAMPLE 4

A mixture of 320 parts of methanol, 70 parts of potassium hydroxide, 100 parts of 1,5-dinitroanthraquinones (98% pure) and 10 parts of amidosulphonic acid is heated to the reflux temperature for 9 hours. After evaporating the reaction mixture, the residue is stirred in 2,000 parts of water, and 70 parts of concentrated HCl, diluted in the ratio 1:1, are added to the resulting suspension. A further 40 parts of amidosulphonic acid are then added. After stirring the mixture for a short time, the solid is filtered off, washed and dried, 89.5 parts of the reaction product being obtained. The content of 1,5-dimethoxyanthraquinone is 94.6%, which corresponds to a yield of about 97% of theory.

EXAMPLE 5

For comparison purposes, the process of Example 4 was repeated, but the reaction was carried out without the addition of amidosulphonic acid. The 88 parts of product obtained in an analogous manner contain only 80% of 1,5-dimethoxyanthraquinone and relatively large amounts of by-products, so that a yield of only about 84% of theory was achieved.

EXAMPLE 6

A solution of 70 parts of potassium hydroxide in 160 parts of methanol is added dropwise to a stirred suspension of 100 parts of 1,8-dinitroanthraquinone (98% pure) in 160 parts of methanol. After adding 25 parts of amidosulphonic acid, the mixture is heated to 68° C. for 14 hours, whilst stirring. After cooling the mixture to room temperature, it is filtered and the residue is washed with water and dried. 84 parts of a yellow product which has crystallised as well-shaped rhomboidal crystals and contains 94.1% of 1,8-dimethoxyanthraquinone are obtained. This corresponds to a yield of 90% of theory.

EXAMPLE 7

100 parts of a mixture of 1,5- and 1,8-dinitroanthraquinone (containing 58.8% of 1,5-dinitroanthraquinone and 39% of 1,8-dinitroanthraquinone) are stirred in 320 parts of methanol. After adding 75 parts of potassium hydroxide and 18 parts of amidosulphonic acid, the mixture is heated to the reflux temperature for about 9 hours. After it has been proved, in a sample, that the reaction is complete, the reaction mixture is concentrated to dryness in a rotary evaporator. The residue is stirred in 1,000 parts of water and treated with an amount of solid amidosulphonic acid such that all the potassium nitrite is destroyed. After filtering off the solid, washing with water and drying, 89.5 parts of a mixture of 1,5- and 1,8-dimethoxyanthraquinone with the following analysis are obtained: 56.2% of 1,5-dimethoxyanthraquinone and 35.6% of 1,8-dimethoxyanthraquinone, which corresponds to yields of 95% and 91% of theory.

EXAMPLE 8

100 parts of 1,x-dinitroanthraquinone (12.3% of 1,5-, 3.2% of 1,6-, 12.7% of 1,7- and 64% of 1,8-dinitroanthraquinone) are introduced into a solution of 50 parts of potassium hydroxide in 400 parts of methanol and the mixture is heated to 120° C. in the course of 2 hours. The mixture is stirred at 120° C. and under 5-6 bars for a further 4 hours and is then distilled to dryness in a rotary evaporator. The residue is stirred in 1,000 parts of water, and about 40 parts of amidosulphonic acid are added until nitrite can no longer be detected. The solid is filtered off, washed with water and dried and 85 parts of 1,x-dimethoxyanthraquinone (81% of 1,5-, 10.9% of 1,6/1,7- and 65% of 1,8 dimethoxyanthraquinone and 4.2% of 1,5/1,8-hydroxymethylanthraquinone) are obtained.

EXAMPLE 9

3 g of a neutral, commercially available emulsifier are dissolved in 160 parts of methanol. 100 g of 1,8-dinitroanthraquinone (98% pure) are introduced, whilst stirring. 240 parts of a potassium methylate solution, which was prepared by stirring 80 parts of potassium hydroxide in 160 parts of methanol, are then added to the suspension thus obtained; the temperature of the reaction mixture is about 30° C. during this addition. After adding 35 parts of amidosulphonic acid, the mixture is heated to 66°-68° C. and left at this temperature for 16 hours, whilst stirring intensively.

After cooling the reaction mixture, the solid is isolated by filtration and purified by washing with methanol and water. After drying, 82 parts of 1,8-dimethoxyanthraquinone with a purity of 99% are obtained. Virtually no nitro derivatives can still be detected. The yield is 92% of theory.

We claim:

1. Process for the preparation of dimethoxyanthraquinones by reacting dinitroanthraquinones with potassium hydroxide in methanol, comprising reacting 1 part by weight of dinitroanthraquinone with 2-8 parts by weight of methanol and 0.5-1.5 parts by weight of potassium hydroxide in the presence of 0.05-0.5 parts by weight of amidosulphonic acid until all the nitro groups have been replaced.

2. Process according to claim 1, wherein 3-5 parts by weight of methanol and 0.6-0.8 parts by weight of potassium hydroxide are employed.

3. Process according to claim 1, wherein the reaction is carried out in the presence of 0.1-0.3 parts by weight of amidosulphonic acid.

4. Process according to claim 1 wherein the reaction is carried out in the temperature range from 50° to 150° C.

5. Process according to claim 1, wherein the reaction is carried out in the temperature range from 60° to 70° C.

6. Process according to claim 1, wherein the dinitroanthraquinone is at least one of 1,5- and 1,8-dinitroanthraquinone obtained from the industrial dinitration of anthraquinone.

7. Process according to claim 1, wherein the dinitroanthraquinone is a mixture obtained from the industrial dinitration of anthraquinone and contains 1,5- and/or 1,8-dinitroanthraquinone.

* * * * *